(12) United States Patent
Gaines et al.

(10) Patent No.: US 8,897,198 B2
(45) Date of Patent: *Nov. 25, 2014

(54) MEDICAL DEVICE WIRELESS NETWORK ARCHITECTURES

(75) Inventors: Robert B. Gaines, Lake Saint Louis, MO (US); Joel D. Wiesner, St. Peters, MO (US); John Holste, Hamburg, IL (US)

(73) Assignee: Covidien LP, Mansfield, MA (US)

( * ) Notice: Subject to any disclaimer, the term of this patent is extended or adjusted under 35 U.S.C. 154(b) by 332 days.

This patent is subject to a terminal disclaimer.

(21) Appl. No.: 13/006,784

(22) Filed: Jan. 14, 2011

(65) Prior Publication Data

US 2012/0182924 A1 Jul. 19, 2012

(51) Int. Cl.
*H04B 7/14* (2006.01)
*G06F 19/00* (2011.01)

(52) U.S. Cl.
CPC ................................ *G06F 19/3418* (2013.01)
USPC ........................................................ 370/315

(58) Field of Classification Search
USPC ................ 370/315–338; 340/286.07, 539.11, 340/12.22; 600/300–301, 365, 407, 532, 600/544; 710/63; 705/337; 235/462.43; 709/217–219; 455/11.1, 16
See application file for complete search history.

(56) References Cited

U.S. PATENT DOCUMENTS

| | | | |
|---|---|---|---|
| 5,451,839 A | 9/1995 | Rappaport et al. | |
| 5,936,539 A | 8/1999 | Fuchs | |
| 6,221,012 B1 | 4/2001 | Maschke et al. | |
| 6,377,162 B1 | 4/2002 | Delestienne et al. | |
| 6,377,806 B1 | 4/2002 | Tokuyoshi | |
| 6,442,433 B1 | 8/2002 | Linberg | |
| 6,519,569 B1 | 2/2003 | White et al. | |
| 6,578,002 B1 | 6/2003 | Derzay et al. | |
| 6,790,198 B1 | 9/2004 | White et al. | |

(Continued)

FOREIGN PATENT DOCUMENTS

| | | |
|---|---|---|
| CA | 2 644 695 | 1/2004 |
| CA | 2 648 885 | 11/2007 |

(Continued)

OTHER PUBLICATIONS

Miche, et al., "The Internet of Vehicles or the Second Generation of Telematic Services", ERCIM News, ERCIM, Paris, FR, vol. 77, Apr. 1, 2009, pp. 43-45.

(Continued)

*Primary Examiner* — Vinncelas Louis
(74) *Attorney, Agent, or Firm* — Lisa E. Winsor, Esq.

(57) ABSTRACT

An architecture for networked communications between a series of medical devices and a remote monitoring device. An interface circuit coupled to each medical device communicates with one of a plurality of relay modules via a wireless relay network. The relay modules communicate with the remote monitoring device over an internet-accessible wireless communication network. Each relay module includes a receiver coupled to the wireless relay network, a first transmitter coupled to the wireless relay network, a second transmitter coupled to the internet-accessible wireless communications network; and a controller. The controller determines a status of the internet-accessible wireless communications network. When the status indicates that the internet-accessible wireless communications network is accessible to the wireless relay module, the second transmitter is selected for transmitting medical device data. When the internet-accessible wireless communications network is not accessible, the first transmitter is selected for transmitting the data to another wireless relay module.

28 Claims, 5 Drawing Sheets

(56) References Cited

U.S. PATENT DOCUMENTS

| | | |
|---|---|---|
| 6,839,753 B2 | 1/2005 | Biondi et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,937,370 B2 | 5/2011 | Hansen |
| 7,942,844 B2 | 5/2011 | Moberg et al. |
| 7,949,404 B2 | 5/2011 | Hill |
| 7,978,062 B2 | 7/2011 | LaLonde et al. |
| 8,002,701 B2 | 8/2011 | John et al. |
| RE42,934 E | 11/2011 | Thompson |
| 8,073,008 B2 | 12/2011 | Mehta et al. |
| 8,095,381 B2 | 1/2012 | Simmons et al. |
| 8,108,543 B2 | 1/2012 | Hansen |
| 8,125,318 B2 * | 2/2012 | Heimbrock et al. ....... 340/12.22 |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,200,195 B2 | 6/2012 | Le Saint et al. |
| 8,214,549 B2 | 7/2012 | Dicks et al. |
| 8,326,648 B2 | 12/2012 | Kenedy et al. |
| 8,373,556 B2 | 2/2013 | LaLonde et al. |
| 8,395,498 B2 | 3/2013 | Gaskill et al. |
| 8,428,722 B2 | 4/2013 | Verhoef et al. |
| 8,515,547 B2 | 8/2013 | Mass et al. |
| 8,587,427 B2 | 11/2013 | LaLonde et al. |
| 8,694,600 B2 | 4/2014 | Gaines et al. |
| 2002/0178126 A1 | 11/2002 | Beck et al. |
| 2002/0198473 A1 | 12/2002 | Kumar et al. |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0185398 A1 | 8/2005 | Scannell, Jr. |
| 2005/0188853 A1 | 9/2005 | Scannell, Jr. |
| 2005/0201300 A1 | 9/2005 | Bridgelall |
| 2005/0243988 A1 | 11/2005 | Barclay et al. |
| 2005/0288571 A1 * | 12/2005 | Perkins et al. ................ 600/407 |
| 2006/0154642 A1 | 7/2006 | Scannell, Jr. |
| 2006/0238333 A1 | 10/2006 | Welch et al. |
| 2007/0106126 A1 | 5/2007 | Mannheimer et al. |
| 2007/0156033 A1 | 7/2007 | Causey, III et al. |
| 2007/0180140 A1 | 8/2007 | Welch et al. |
| 2007/0186923 A1 | 8/2007 | Poutiatine et al. |
| 2007/0216764 A1 | 9/2007 | Kwak |
| 2007/0230197 A1 | 10/2007 | Scannell, Jr. |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255250 A1 | 11/2007 | Moberg et al. |
| 2007/0258395 A1 | 11/2007 | Jollota et al. |
| 2007/0268687 A1 | 11/2007 | Scannell, Jr. |
| 2007/0276270 A1 | 11/2007 | Tran |
| 2008/0004907 A1 | 1/2008 | Bayne |
| 2008/0012761 A1 | 1/2008 | Derrick et al. |
| 2008/0071234 A1 | 3/2008 | Kelch et al. |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0108880 A1 | 5/2008 | Young et al. |
| 2008/0183502 A1 | 7/2008 | Dicks et al. |
| 2008/0224852 A1 | 9/2008 | Dicks et al. |
| 2008/0281168 A1 | 11/2008 | Gibson et al. |
| 2009/0019061 A1 | 1/2009 | Scannell, Jr. |
| 2009/0023391 A1 | 1/2009 | Falck |
| 2009/0058635 A1 * | 3/2009 | LaLonde et al. ......... 340/539.11 |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0073694 A1 | 3/2009 | Scannell, Jr. |
| 2009/0105549 A1 | 4/2009 | Smith et al. |
| 2009/0115628 A1 | 5/2009 | Dicks et al. |
| 2009/0128320 A1 | 5/2009 | Needham et al. |
| 2009/0184835 A1 | 7/2009 | Deaver, Sr. et al. |
| 2009/0203329 A1 | 8/2009 | White et al. |
| 2009/0234672 A1 | 9/2009 | Dicks et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2009/0306747 A1 | 12/2009 | Fischer et al. |
| 2010/0011000 A1 | 1/2010 | Chakara et al. |
| 2010/0027518 A1 | 2/2010 | Wang |
| 2010/0077115 A1 * | 3/2010 | Rofougaran ................... 710/63 |
| 2010/0079276 A1 | 4/2010 | Collins et al. |
| 2010/0080200 A1 | 4/2010 | Stewart |
| 2010/0082371 A1 | 4/2010 | Kamp et al. |
| 2010/0085948 A1 | 4/2010 | Yu et al. |
| 2010/0117835 A1 | 5/2010 | Nanikashvili |
| 2010/0138235 A1 | 6/2010 | Marks et al. |
| 2010/0166170 A1 | 7/2010 | East |
| 2010/0198142 A1 | 8/2010 | Sloan et al. |
| 2010/0217723 A1 * | 8/2010 | Sauerwein et al. ........... 705/337 |
| 2010/0219250 A1 * | 9/2010 | Wang ...................... 235/462.43 |
| 2010/0234695 A1 | 9/2010 | Morris |
| 2010/0260061 A1 | 10/2010 | Bojahra et al. |
| 2010/0279647 A1 | 11/2010 | Jacobs et al. |
| 2010/0292556 A1 | 11/2010 | Golden |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1 | 6/2011 | Eaton et al. |
| 2011/0158430 A1 | 6/2011 | Dicks et al. |
| 2011/0161111 A1 | 6/2011 | Dicks et al. |
| 2011/0179405 A1 | 7/2011 | Dicks et al. |
| 2011/0255454 A1 | 10/2011 | Hauser et al. |
| 2011/0270045 A1 | 11/2011 | Lebel et al. |
| 2011/0273287 A1 | 11/2011 | LaLonde et al. |
| 2011/0280224 A1 | 11/2011 | Falck et al. |

(56) References Cited

U.S. PATENT DOCUMENTS

| | | |
|---|---|---|
| 2011/0282671 A1 | 11/2011 | Dicks et al. |
| 2011/0292862 A1 | 12/2011 | Shimizu |
| 2012/0004925 A1 | 1/2012 | Braverman et al. |
| 2012/0108917 A1 | 5/2012 | Libbus et al. |
| 2012/0182143 A1 | 7/2012 | Gaines et al. |
| 2012/0182894 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0066644 A1 | 3/2013 | Dicks et al. |
| 2013/0147622 A1 | 6/2013 | LaLonde et al. |
| 2013/0154851 A1 | 6/2013 | Gaskill et al. |
| 2013/0162426 A1 | 6/2013 | Wiesner et al. |
| 2013/0278414 A1 | 10/2013 | Sprigg et al. |
| 2013/0310896 A1 | 11/2013 | Mass |
| 2014/0009271 A1 | 1/2014 | Collins et al. |
| 2014/0062718 A1 | 3/2014 | LaLonde et al. |
| 2014/0142979 A1 | 5/2014 | Mitsunaga |
| 2014/0152466 A1 | 6/2014 | Wiesner et al. |

FOREIGN PATENT DOCUMENTS

| | | |
|---|---|---|
| CA | 2 644 635 | 8/2008 |
| CN | 101601040 A | 12/2009 |
| EP | 2227063 A1 | 9/2010 |
| JP | 2003109160 | 4/2003 |
| JP | 2006520657 | 9/2006 |
| JP | 2007531442 | 11/2007 |
| JP | 2008108170 | 5/2008 |
| JP | 2009-535715 A | 1/2009 |
| JP | 2010-524050 A | 7/2010 |
| JP | 2011-502369 A | 1/2011 |
| KR | 10-2008-0016458 A | 2/2008 |
| KR | 10-2009-0122968 A | 12/2009 |
| KR | 10-2010-0028318 A | 3/2010 |
| WO | WO 94/16617 | 8/1994 |
| WO | WO 98/14228 A1 | 4/1998 |
| WO | WO 03/018919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2005/057294 | 6/2005 |
| WO | WO 2005/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2008/052034 A1 | 5/2008 |
| WO | WO 2008/097316 A1 | 8/2008 |
| WO | WO 2009/032134 A2 | 3/2009 |
| WO | WO 2009/063303 A1 | 5/2009 |

OTHER PUBLICATIONS

Kawai et al., "Proposal of an Assured Corridor Mechanism for Urgent Information Transmission in Wireless Sensor Networks", IEICE Trans. on Commun., vol. E90B, No. 10, Oct. 1, 2007, pp. 2817-2826, XP001508610.
International Search Report and Written Opinion of the International Searching Authority for PCT/US2012/021007, dated Sep. 20, 2012, 19 pages.
International Search Report and Written Opinion of the International Searching Authority for PCT/US2012/068895, dated Mar. 15, 2013, 15 pages.
International Search Report and Written Opinion of the International Searching Authority for PCT/US2012/068892, dated Apr. 1, 2013, 12 pages.
International Search Report and Written Opinion of the International Searching Authority for PCT/US2013/020069, dated Feb. 1, 2013, 9 pages.
International Search Report and Written Opinion of the International Searching Authority for PCT/US2013/020071, dated Feb. 1, 2013, 10 pages.
International Search Report and Written Opinion of the International Searching Authority for PCT/US2012/068888, dated Apr. 1, 2013, 15 pages.
International Search Report and Written Opinion of the International Searching Authority for PCT/US2012/025906, dated Dec. 3, 2012, 21 pages.
Office Action dated Nov. 16, 2012 for U.S. Appl. No. 13/037,886, filed Mar. 1, 2011, 19 pages.
Response to Office Action dated Nov. 16, 2012 for U.S. Appl. No. 13/037,886, filed Feb. 15, 2013.
Atmel Corporation, "ZigBee PRO Stack and Software Development Kit," Nov. 4, 2011.
Bacheldor, "Hospital Tries ZigBee to Track Patients," RFID Journal, Jul. 21, 2006.
BelAir Networks, "Capacity of Wireless Mesh Networks," white paper, 2006.
Bogia, "Enabling the future of u-Health-IEEE 11073 Personal Health Device Standards," slides, Sep. 16, 2009.
Bowman, "Newly Ratified ZigBee Health Care Profile Now Available for Public Download," Apr. 6, 2010.
Craig, "ZigBee Networks," Apr. 1, 2005.
Craig, "ZigBee: 'Wireless Control That Simply Works'," prior to Jan. 2011.
Digi International Inc., "ConnectPort® X4 H," retrieved from the Internet.
Digi International Inc., "Demystifying 802.15.4 and ZigBee®," white paper, 2008-2010.
Digi International Inc., "XBee® & XBee-PRO® ZB," retrieved from the Internet: 2008-2010.
Digi International Inc., "XBee® & XBee-PRO® ZB ZigBee® PRO RF Modules," Nov. 2, 2010.
Dvorak, "Remote Monitoring," Apr. 1, 2005.
ENP Newswire, "Freescale products achieve ZigBee Health Care Certification," May 19, 2010.
Huang, "Medical electronics: from hospital and clinic to the home," Dec. 8, 2010.
ICP DAS, "ZigBee Converter User's Manual," Sep. 22, 2008.
Le, "Designing a ZigBee-ready IEEE 802.15.4-compliant radio transceiver," Nov. 2004.
Norris et al., "Single-chip ZigBee for Indoor Mobile Telemetry," presentation, Jun. 21, 2005.
Pinto, "WMM-Wireless Mesh Monitoring," Technical report, 2009.
Sailhan et al., "Wireless Mesh Network Monitoring: Design, Implementation and Experiments," In proc. of IEEE Workshop on Distributed Autonomous Network Management (DANMS), 2007.
Skibniewski et al, "Ubiquitous Computing: Object Tracking and Monitoring Inconstruction Processes Utilizing Zigbee™ Networks," The 23th International Symposium on Automation and Robotics in Construction (ISARC2006), Oct. 3-5, Tokyo, Japan.
Stewart, "Build reliable Zigbee-based solutions," EE Times-Asia, Apr. 16-30, 2007.
Texas Instruments, "Choose your ZigBee solution with TI," 1Q 2010.
Texas Instruments, "Consumer Medical Applications Guide," 2010.
Texas Instruments, "RF/IF and ZigBee® Solutions," Dec. 8, 2010.
Texas Instruments, "ZigBee® Wireless Networking Overview," 1 page, 2010.
The Silicon Horizon Inc., "techFX Zigbee rev A-techFX Zigbee Tools v 1.0," 2007-2008.
Tutorial-Reports.com, "Zigbee Tutorial," Nov. 1, 2010.
Unknown author, "The Nokia Network Monitor Introduction," Oct. 30, 2005.
Versel, "ZigBee Alliance ratifies wireless protocol for low-power medical devices," Apr. 6, 2010.
Wellspring, "Router, Gateway, Base Station, Cell Modem Specification and Submittal," 5 pages, prior to Jan. 2011.
Wellspring, "Wellspring Switches to a ZigBee-Cellular Hybrid System," press release, Feb. 20, 2006.

(56) References Cited

OTHER PUBLICATIONS

ZigBee Alliance, "ZigBee Wireless Sensor Applications for Health, Wellness and Fitness," Mar. 2009.
Office Action dated May 22, 2013; for U.S. Appl. No. 13/037,886; 14 pages.
PCT Search Report and Written Opinion of the ISA; dated Apr. 29, 2013; for PCT Pat. App. No. PCT/US2013/021530; 10 pages.
Response filed Jul. 12, 2013, to Final Office Action dated May 22, 2013; for U.S. Appl. No. 13/037,888; 14 pages.
Article 19 Amendment; dated Nov. 16, 2012; for PCT Pat. App. No. PCT/US2012/021007; 7 pages.
Article 19 Amendment; dated Feb. 4, 2013; for PCT Pat. App. No. PCT/US2012/025906; 9 pages.
PCT International Preliminary Report on Patentability, dated Jul. 25, 2013; for PCT Pat. App. No. PCT/US2012/021007; 12 pages.
PCT International Search Report; dated Aug. 2, 2012; for PCT Pat. App. No. PCT/US2012/021008.
PCT International Preliminary Report on Patentability; dated Jul. 25, 2013; for PCT Pat. App. No. PCT/US2012/021008; 7 pages.
Notice of Allowance; dated Oct. 9, 2013; for U.S. Appl. No. 13/037,886; 11 pages.
Office Action dated Sep. 5, 2013, for U.S. Appl. No. 13/006,769, 36 pages.
PCT International Preliminary Report on Patentability of the ISA; dated Sep. 12, 2013; for PCT Pat. App. No. PCT/US2012/025906; 14 pages.
Notification Concerning Transmittal of International Preliminary Report on Patentability (including the IPRP and Written Opinion of the ISA) dated Jul. 25, 2013; for International Appl. No. PCT/US2012/021008; 7 pgs.
Office Action dated May 27, 2014; for U.S. Appl. No. 13/334,463; 48 pages.
Mexican Notice of Allowance dated May 7, 2014; for Mexican Pat. App. No. MX/a/2013/009985; 2 pages.
Response with Terminal Disclaimer filed Jul. 30, 2014; to Office Action dated Jun. 20, 2014; for U.S. Appl. No. 13/334,447; 15 pages.
Response with Terminal Disclaimer filed Jul. 30, 3014; to Office Action dated Jun. 23, 2014; for U.S. Appl. No. 13/334,459: 13 pages.
Response filed Jul. 30, 3014; to Final Office Action dated Jun. 16, 2014; to U.S. Appl. No. 13/353,565; 22 pages.
Response filed Aug. 4, 2014; to Office Action dated May 27, 2014; for U.S. Appl. No. 13/334,463; 21 pages.
Mexican Response to Office Action received Jul. 29, 2014; for Mexican Pat. App. No. Mx/a/2013/008157; 14 pages
PCT International Preliminary Report on Patentability dated Jul. 3, 2014; for PCT Pat. App. No. PCT/US2012/068895; 10 pages.
Final Office Action dated Aug. 6, 2014; for U.S. Appl. No. 13/352,608; 38 pages.
PCT International Preliminary Report on Patentability of the ISA dated Jul. 31, 2014; for PCT Pat. App. No. PCT/US2013/020069; 6 pages.
PCT International Preliminary Report on Patentability of the ISA dated Jul. 31, 2014; for PCT Pat. App. No. PCT/US2013/020071; 6 pages.
Singapore Written Opinion dated Jul. 25, 2014; for Singapore Pat. App. No. 2013053244; 7 pages.
Office Action dated Jun. 16, 2014 for U.S. Appl. No. 13/353,565, filed Jan. 19, 2012.
Japanese Office Action dated May 30, 2014 for Application No. 2013-549531.
Notice of Allowance for U.S. Appl. No. 13/352,575, filed Jan. 18, 2012.
Office Action dated Jun. 20, 2014 for U.S. Appl. No. 13/334,447, filed Dec. 22, 2011.
European Search Report dated Jun. 14, 2014; for European Patent Application No. 14168075.1-1951; 8 pages.
Office Action dated Jun. 23, 2014 for U.S. Appl. No. 13/334,459, filed Dec. 22, 2011 44 pages.
Response filed (with English Language Passage) of Mexican Office Action received Jul. 7, 2014; for Mexican Pat. App. No. MX/a/2013/008154; 16 pages.
Response filed Feb. 18, 2014; to Office Action dated Sep. 27, 2013; for U.S. Appl. No. 13/241,620; 24 pages.
Response filed Feb. 13, 2014; to Office Action dated Sep. 5, 2013; for U.S. Appl. No. 13/006,769; 18 pages.
Response filed Feb. 18, 2014 for Office Action dated Sep. 27, 2013 for U.S. Appl. No. 13/241,620; 24 pages.
Response filed Feb. 13, 2014 for Office Action dated Sep. 5, 2013 for U.S. Appl. No. 13/006,769; 18 pages.
European Response filed Mar. 3, 2014; to Official Communication dated Aug. 22, 2013; and to the Written Opinon; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.
Notice of Allowance dated Apr. 30, 2014; for U.S. Appl. No. 13/241,620; 21 pages.
Office Action dated Apr. 29, 2014; for U.S. Appl. No. 13/352,608; 50 pages.
Mexican Official Action received May 2, 2014, for Mexican Pat. App. No. MX/A2013/008157; 3 pages.
U.S. Response to 312 Amendment dated Jul. 21, 2014; for U.S. Appl. No. 14/154,285; 3 pages.
Japanese Office Action (including English translation) dated Jun. 23, 2014; for Japanese Pat. App. No. 2013-549532 6 pages.
PCT International Preliminary Report on Patentability of the ISA dated Jul. 3, 3014; for PCT Pat. App. No. PCT/US2012/068892; 8 pages.
PCT International Preliminary Report on Patentability of the ISA dated Jul. 3, 2014; for PCT Pat. App. No. PCT/US2012/068888; 8 pages.
Singapore Written Opinion dated Jun. 18, 2014; for Singapore Pat. App. No. 2013053236; 11 pages.
Singapore Written Opinion dated Jun. 19, 2014; for Singapore Pat. App. No. 2013065230; 22 pages.
Office Action dated Sep. 9, 2014; for U.S. Appl. No. 13/353,565; 24 pages.
Gaines et al. "Improved Wireless Relay Module for Remote Monitoring Systems;" U.S. Appl. No. 14/308,881, filed Jun. 19, 2014; 36 pages.
Canadian Office Action dated Aug. 4, 2014; for Canadian Pat. App. No. 2,823,600; 3 pages.
PCT Search Report and Written Opinion of the ISA dated Apr. 29, 2013; for PCT Pat. App. No. PCT/US2013/021530; 10 pages.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed Jan. 18, 2012.
Notice of Allowance dated Jun. 6, 2014 for U.S. Appl. No. 14/154,285, filed Jan. 14, 2014.
Notice of Allowance dated Jun. 9, 2014 for U.S. Appl. No. 13/006,769, filed Jan. 14, 2011.
U.S. Appl. No. 14/308,881, filed Jun. 19, 2014, Gaines, et al.
Notice of Allowance dated Aug. 20, 2014, for U.S. Appl. No. 13/334,447; 25 pages.
Notice of Allowance dated Aug. 15, 2014; for U.S. Appl. No. 13/334,459; 20 pages.
PCT International Preliminary Report on Patentability and Written Opinion of the ISA dated Jul. 31, 2014; for PCT Pat. App. No. PCT/US2013/021530; 8 pages.
U.S. Appl. No. 14/462,025, filed Aug. 18, 2014, Wiesner et al.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.

(56) References Cited

OTHER PUBLICATIONS

Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
Request for Continued Examination filed on Jan. 24, 2014; for U.S. Appl. No. 13/037,886; 2 pages.
European Comments on Written Opinion dated Nov. 8, 2013; for EP Pat. App. No. 12708203.0; 2 pages.
Office Action dated Dec. 27, 2013; for U.S. Appl. No. 13/352,575; 31 pages.
Office Action dated Jan. 7, 2014; for U.S. Appl. No. 13/353,565; 33 pages.

\* cited by examiner

MEDICAL DEVICE WIRELESS NETWORK ARCHITECTURES

RELATED APPLICATION

This application is related to U.S. application Ser. No. 13/006,769, now issued as U.S. Pat. No. 8,818,260, filed Jan. 14, 2011, entitled "Wireless Relay Module for Remote Monitoring Systems."

FIELD OF THE INVENTION

The present application is directed to network architectures for providing networked communications between a series of medical devices and remote monitoring devices, and more particularly, to network architectures for providing networked communications between a series of medical devices and remote monitoring devices via wireless relay networks and internet-accessible wireless communications networks.

BACKGROUND OF THE INVENTION

In critical care and home care health service centers including hospitals, clinics, assisted living centers and the like, care giver-patient interaction time is at a premium. Moreover, response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

Clearly, for improved efficiencies in centralized monitoring of critical care and home care health service centers, it may be desirable to provide a single "off-site" centralized monitoring location for monitoring several geographically-dispersed critical care health service centers.

One alternative to conventional WiFi or IEEE 802.11-based local area networks, are ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are generally unusable for centralized monitoring locations located off-site. Also, in accordance with applicable patient data privacy provisions of the Health Insurance Portability and Accountability Act of 1996 (HIPAA), it would be desirable to provide a network architecture that addresses secure transmission of information between the monitored medical devices and the central monitoring location.

Thus, it would be desirable to provide a network architecture for centralized monitoring of medical devices that couples wireless personal area networks in communication with remote monitored medical devices that overcome the disadvantages of the previously described prior art network architectures.

SUMMARY OF THE INVENTION

The present invention is directed to network architectures for providing networked communications between a series of medical devices and remote monitoring devices. In accordance with a preferred embodiment of the invention, one or more medical devices including, for example, enteral feeding, thermometers, pulse oximeters, respirators, blood pressure monitors, pulse monitors, weight scales and glucose meters) are provided at a patient facility. An interface circuit is coupled to each medical device, and is configured for communicating with one of a plurality of wireless relay modules via a wireless relay network. The wireless relay modules are further configured to communicate with a remote monitoring device over an internet-accessible wireless communication network, and preferably, a wireless wide-area network (WWAN) such as a mobile telephone data network, e.g. 3G or 4G network. Also, for compliance for example with HIPAA regulations, communications over each of the wireless networks are preferably conducted securely.

Each of the plurality of wireless relay modules includes a receiver capable of wirelessly receiving medical device data from respective interface circuits via the wireless relay network, a first transmitter capable of wirelessly transmitting medical device data to another one of the wireless relay modules over the wireless relay network, a second transmitter capable of wirelessly transmitting data over an internet-accessible wireless communications network; and a controller coupled to the first and second transmitters. The controller is configured to determine access status of the internet-accessible wireless communications network, and to select one of the first or second transmitters based on that status. For example, when the status indicates that the interne-accessible wireless communications network is accessible to the wireless relay module, the controller selects the second transmitter for transmitting medical device data transmitted by the interface circuit to the internet-accessible wireless communications network. When the status indicates that the internet-accessible wireless communications network not accessible, the controller selects the first transmitter for transmitting the medical device data to another one of the wireless relay modules. In this manner, additional attempts to transmit the medical device data over the internet-accessible wireless communication network can be attempted by this other wireless relay module (and potentially additional ones of the wireless relay modules) until a successful transmission is achieved.

The wireless relay module may also advantageously communicate its status and the status of other wireless relay modules via the wireless relay network and over the internet-accessible wireless communications network. In addition, the wireless relay module may further include a second receiver for receiving data and commands from the internet-accessible wireless communications network for communicating to specific interface circuits and corresponding medical devices.

BRIEF DESCRIPTION OF THE DRAWINGS

The invention will become more readily apparent from the Detailed Description of the Invention, which proceeds with reference to the drawings, in which.

DETAILED DESCRIPTION OF THE INVENTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-5.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
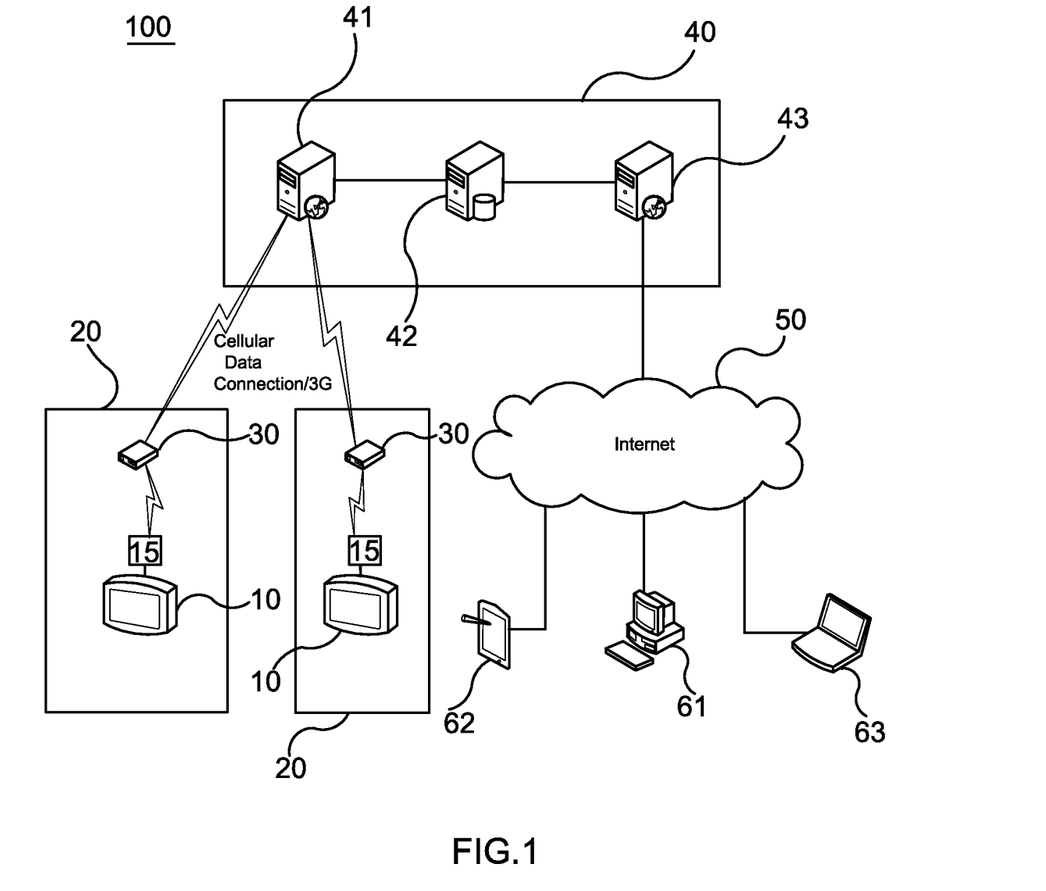
FIG. 1 present a schematic diagram of an exemplary architecture for a system for monitoring medical devices according to the present invention.

A schematic diagram of an exemplary architecture 100 for a system for monitoring medical devices in accordance with the present invention is illustrated in FIG. 1. One or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may attached to or worn by an ambulatory patient. Associated with each medical device 10 is an interface circuit interface circuit 15 that includes a transceiver for transmitting and receiving signals in a facility-oriented wireless network such as, for example, a Low-Rate Wireless Personal Area Networks or "LR-WPAN," ZIGBEE network or other low-power personal area networks such as the low power Bluetooth networks, e.g., Bluetooth 2.0, existing or presently under development or consideration. It should be understood that interface circuit 15 may be contained within or disposed external to medical device 10 in accordance with the present invention. Also provided within the patient facility 20 are one or more relay modules 30

Figure 2:
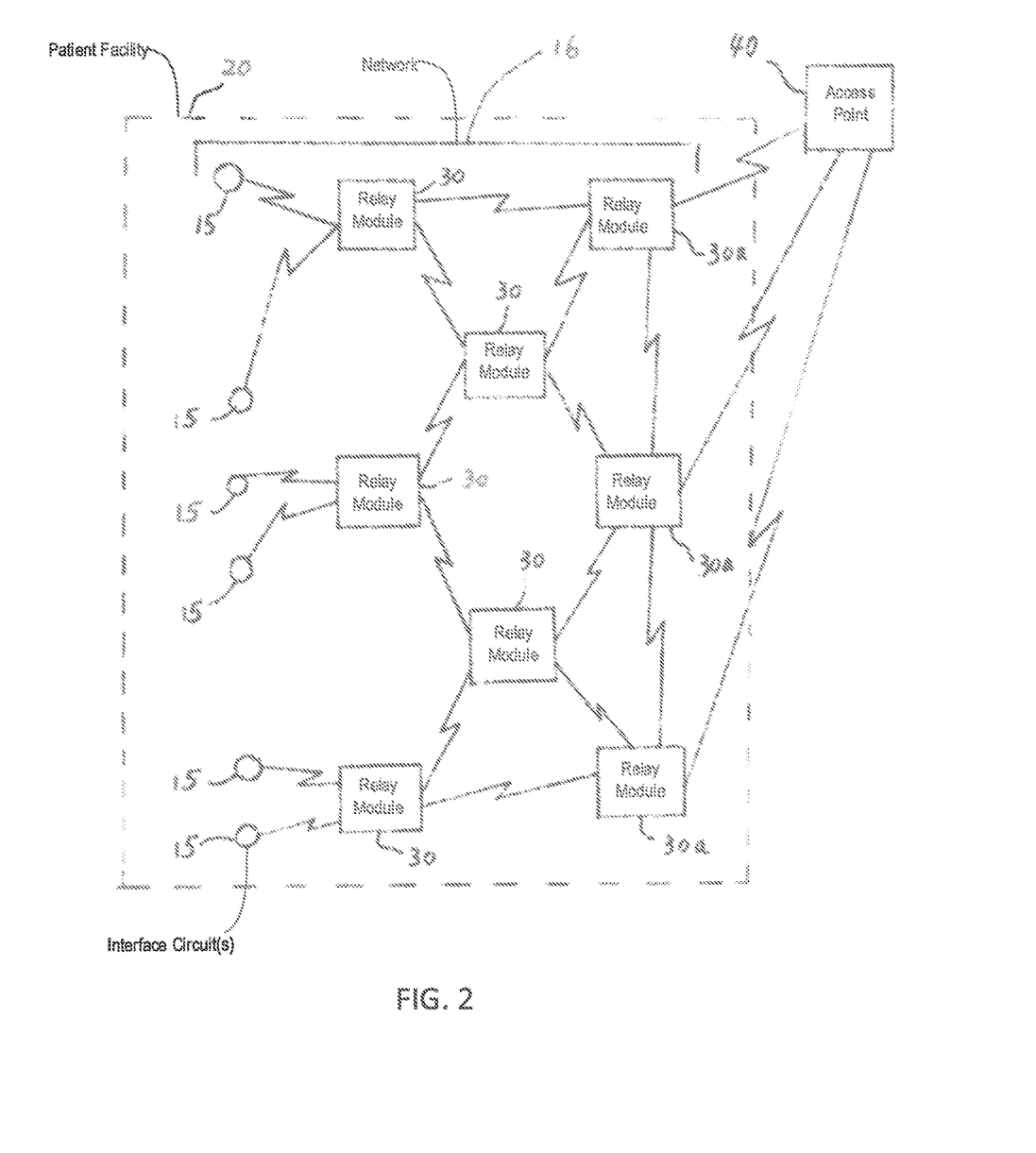
FIG. 2 presents a schematic diagram further illustrating exemplary wireless network components of the architecture according to FIG. 1.
Figure 3:
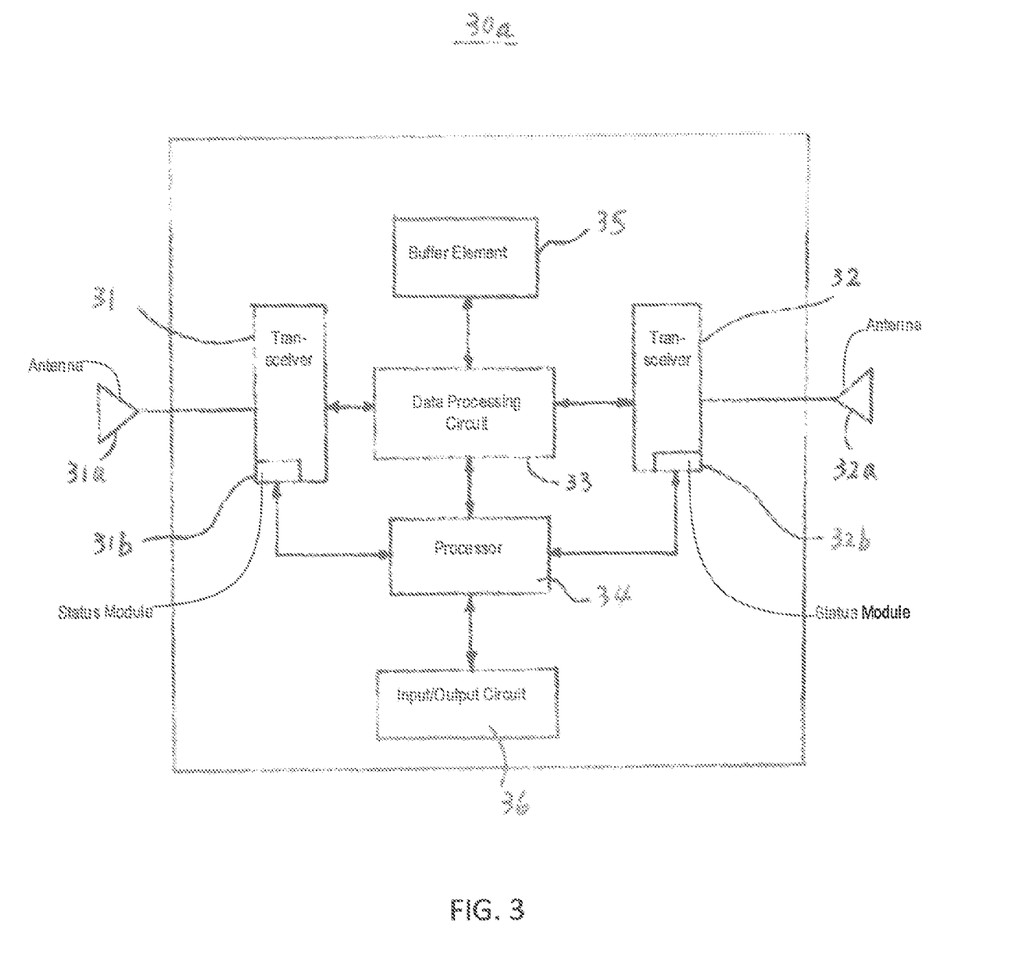
FIG. 3 presents a schematic diagram illustrating an exemplary wireless relay module associated with the architecture according to FIG. 1.

As described in greater detail with regard to FIG. 3, each module 30 includes a first transceiver for receiving signals from and transmitting signals to the interface circuits 15 in the facility-oriented wireless network. Relay modules 30a as depicted in FIG. 3 correspond to relay modules 30, and further include a second transceiver for wirelessly transmitting signals to and receiving signals from an access point 40 as shown in FIG. 2 via a wireless wide-area network or "WWAN". Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union-Radiocommunication Sector (ITU-R). For compliance with HIPAA regulations, communications over each of the facility-oriented wireless network and WWAN are preferably conducted securely using, for example, using a Secure Sockets Layer (SSL) protocol or a Transport Layer Security (TLS) protocol.

As illustrated in FIG. 1, a suitable access point 40 useable with the present invention may include an inbound web server 41 that incorporates or otherwise has access to a transceiver for communicating with the relay modules 30a over the WWAN. Medical device data received by the inbound web server 41 over the WWAN is forwarded to a secure data storage server 42, which is configured for example to log the received data in association with identification information of the associated medical devices. An outbound web server 43 is configured, for example, to receive and qualify data retrieval requests submitted by one or more of remote monitoring devices 61, 62 and 63 over a broad-band network 50 (for example, over the Internet), to request associated medical device data to be retrieved from the secure data storage server 42, and to format and transmit the retrieved data to the one or more remote monitoring devices 61, 62 and 63 for display on associated device displays. While this disclosed architecture for the access point 40 is illustrated with an exemplary embodiment of the present invention, it should be understood that any architecture for the access point 40 that enables the receipt, storage and retrieval of medical device data on a device display of the one or more remote monitoring devices 61, 62 and 63 is intended to be included within the scope of the present invention.

FIG. 2 presents a block diagram that further illustrates exemplary components of the inventive architecture that are located within or otherwise associated with the patient facility 20 of FIG. 1. In FIG. 2, a number of interface circuits 15 and relay modules 30, 30a are arranged in a mesh network 16 within the patient facility 20. The interface circuits 15 and relay modules 30, 30a are configured to communicate with one another via associated wireless links. In a preferred embodiment of the present invention represented in FIG. 2, the network 16 is a ZIGBEE mesh network based on IEEE 802.15.4. However, the network 16 may be organized according to a variety of other wireless local area network (WLAN) or WPAN formats including, for example, WiFi WLANs based on IEEE 802.11 and BLUETOOTH WPANs based on IEEE 802.15.1.

In the illustrated ZIGBEE mesh network 16, each of the interface circuits 15 includes a communications interface such as, for example, a wired communications interface, to an associated medical device 10. In addition, each of the relay modules 30, 30a includes at least one transceiver configured to communicate with other relay modules 30, 30a in the ZIGBEE mesh network 16. Relay modules 30a further include at least a second transceiver for communicating over the WWAN with the access point 40.

The ZIGBEE mesh network 16 provides the advantages of being self-configurable when one or more interface circuits 15 and/or relay modules 30, 30a are added to the network, and self-healing when one or more interface circuits 15 and/or relay modules 30, 30a are removed from or otherwise disabled in the network. Sub-groupings of the interface circuits 15 and relay modules 30, 30a may be provided in a defined geographic space (for example, on an individual floor or within a region of a floor in a multi-floor home or care facility).

FIG. 3 provides a block diagram illustrating exemplary components of relay module 30a. The relay module 30a of FIG. 3 includes a first transceiver 31 for wirelessly communicating with interface circuits 15 and other relay modules 30, 30a in the WLAN or WPAN network 16 of FIG. 2 via an antenna 31a. The relay module 30a further includes a second transceiver 32 for wirelessly communicating with the access point 40 over the WWAN via an antenna 32a. Each of the transceivers 31, 32 is in communication with a data processing circuit 33, which is configured to operate under the control of a processor 34 to accept data received by the transceivers 31, 32 and store the received data in a buffer element 35. In addition, the data processing circuit 33 is further configured to retrieve data from the buffer element 35 under the direction of the processor 34 and provide the retrieved data to a selected one of the transceiver 31 or transceiver 32 for transmission. In order to make a selection, the processor 34 is configured to communicate with respective status modules 31b, 32b of the transceivers 31, 32 in order to determine a communications status of each of the transceivers 31, 32.

The processor 34 is also preferably in communication with an input/output circuit 36, which provides signals to one or more display elements (not shown) of the relay module 30a, for example, for indicating a start-up or current status of the relay module 30a, including communication or connection status with the WLAN or WPAN network 16 and WWAN. The input/output circuit 36 may also be connected to user buttons, dials or input mechanisms and devices of module 30a. The input/output circuit 36 is further usable for providing alarm signals to indicate, for example, A/C power loss or loss of accessibility to the WWAN or wireless relay network.

Relay module 30a may preferably be provided as a small physical enclosure (not shown) with an integral power plug and power supply circuit, such that the relay module 30a may be directly plugged into and supported by a conventional wall outlet providing commercial A/C power. Relay module 30a may also preferably include a battery back-up circuit (not shown) to provide uninterrupted power in the event of A/C power outage as well as for ambulatory use of the relay module. Alternatively, relay module 30a may be provided with rechargeable and/or replaceable battery power as a primary power source for ambulatory use.

Figure 4:
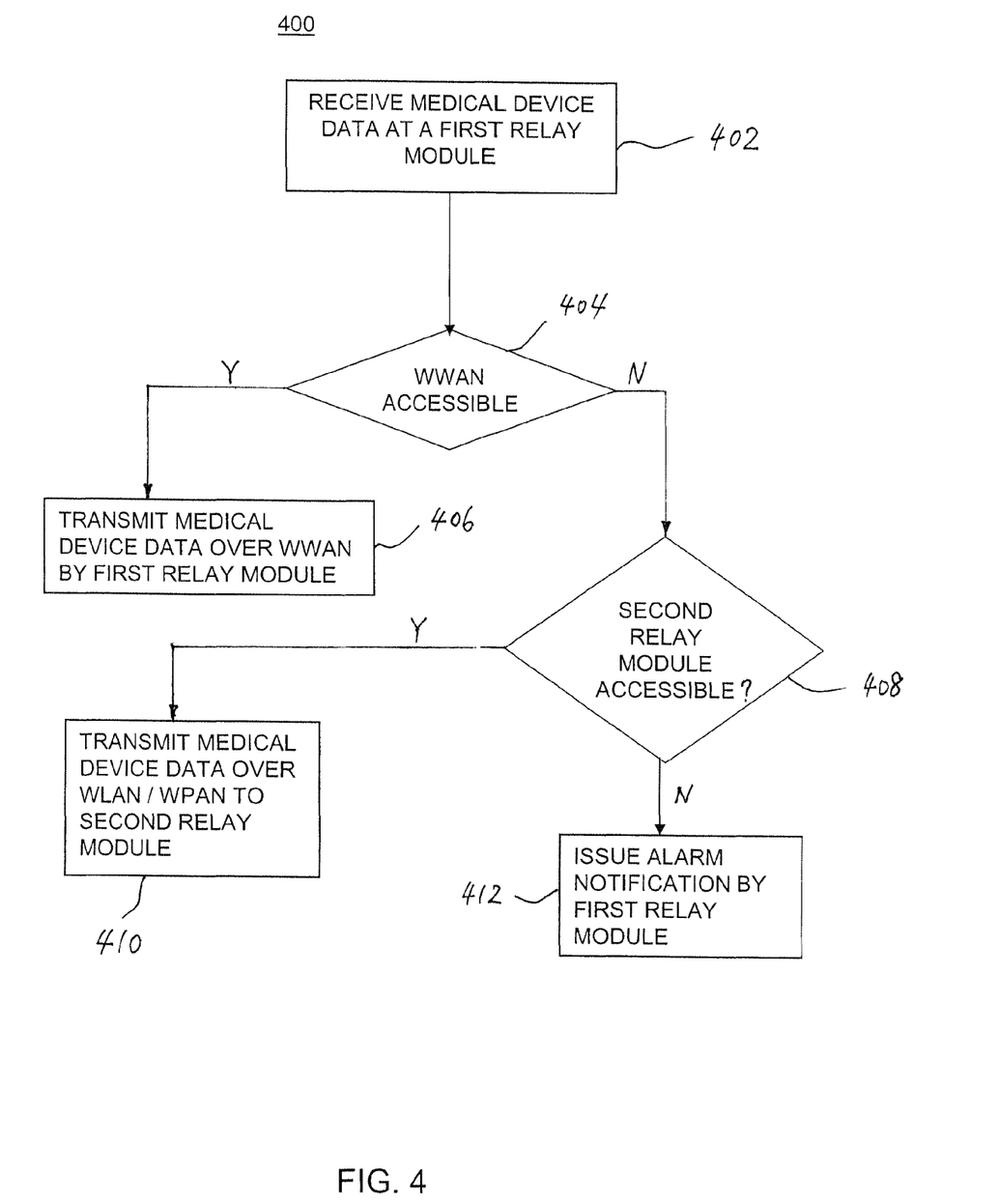
FIG. 4 presents a flow diagram illustrating a first exemplary method of operation for the architecture according to FIG. 1.

FIG. 4 presents a flow diagram illustrating an exemplary method of operation 400 for the architecture according to FIG. 1 and relay module 30, 30a components of FIGS. 2, 3, relating to the transmission of medical device data obtained from a medical device 10 to the access point 40. At step 402 of the method 400, the medical device data is received at a first one of the relay modules 30a from one of the interface circuits 15 and/or other relay modules 30, 30a over the ZIGBEE mesh network 16. At step 404, the processor 34 of the one relay module 30a determines whether the WWAN is accessible by that relay module 30a.

The determination of step 404 may be carried out in a variety of manners. For example, the processor 34 may interrogate the status module 32b of the transceiver 32 at the time of the receipt of the medical device data to determine a status of access for the transceiver 32 to the WWAN (for example, as the result of the transceiver 32 detecting an access signal of the WWAN having adequate signal strength). Alternatively, the processor 34 may interrogate the status module 32b at a different time including, for example, at system start-up and/or periodically (for example, hourly), and maintain a status indicator such as in the buffer 35 or another storage element to be retrieved at the time of receipt of the medical data. As yet another alternative, the relay module 30, 30a may be assigned a predetermined, fixed role within the network 16. For example, relay modules 30a in the network 16 may be assigned a data routing assignments by a controller or "master" relay module. By definition, the WWAN status for relay module 30 that does not possess WWAN access capability shall have a fixed status of "WWAN inaccessible."

If, as provided for in step 404, the status module 32b indicates that the WWAN is accessible by the transceiver 32, then the processor 34 will proceed to step 406 to instruct the data processing circuit 33 of the one relay module 30 to retrieve the medical device data from the buffer 35 (as necessary) and forward the medical device data to the transceiver 32 for transmission to the access point 40 over the WWAN.

Alternatively, in step 404, the status module 32b may indicate that the WWAN is not accessible by the transceiver 32. For example, if the one relay module 30a is located on a basement floor of the building in an area that is substantially shielded with respect to WWAN signals, the WWAN may not be accessible to the one relay module 30a. In this event, at step 408, the processor 34 determines whether a second relay module 30a is accessible via the WLAN or WPAN, Again, this determination may be made in a variety of manners including by instructing the transceiver 31 to send a handshake signal transmission directed to a second relay module 30a and to listen for a reply, or by retrieving a stored status indicator for the second relay module 30a.

If the second relay module 30a is accessible, then the processor 34 instructs the data processing circuit 33 of the one relay module 30a to retrieve the medical device data from the buffer 35 (as necessary) and forward the medical device data to the transceiver 31 for transmission to the second relay module 30a over the WLAN or WPAN at step 410. Alternatively, if the second relay module 30a is inaccessible in step 408, this portion of the process 400 may preferably be repeated to search for a further relay module 30a that is accessible. Alternatively, or in the event that no other relay module 30a is available, the processor 34 of the one relay module 30a may preferably issue an alarm notification at step 412. Such an alarm notification may, for example, include one or more of local visual and audio alarms as directed by processor 34 via the input/output circuit 36 of the one relay module 30a, alarm messages directed by the processor 34 to another accessible WPAN, WLAN or WWAN via one or more of the transceivers 31, 32, and/or alarm messages generated by the inbound web server 41 of the access point 40 of FIG. 1 after a specified time period has been exceeded during which a handshake signal of the relay module 30a is due to be received at the inbound web server 41.

Figure 5:
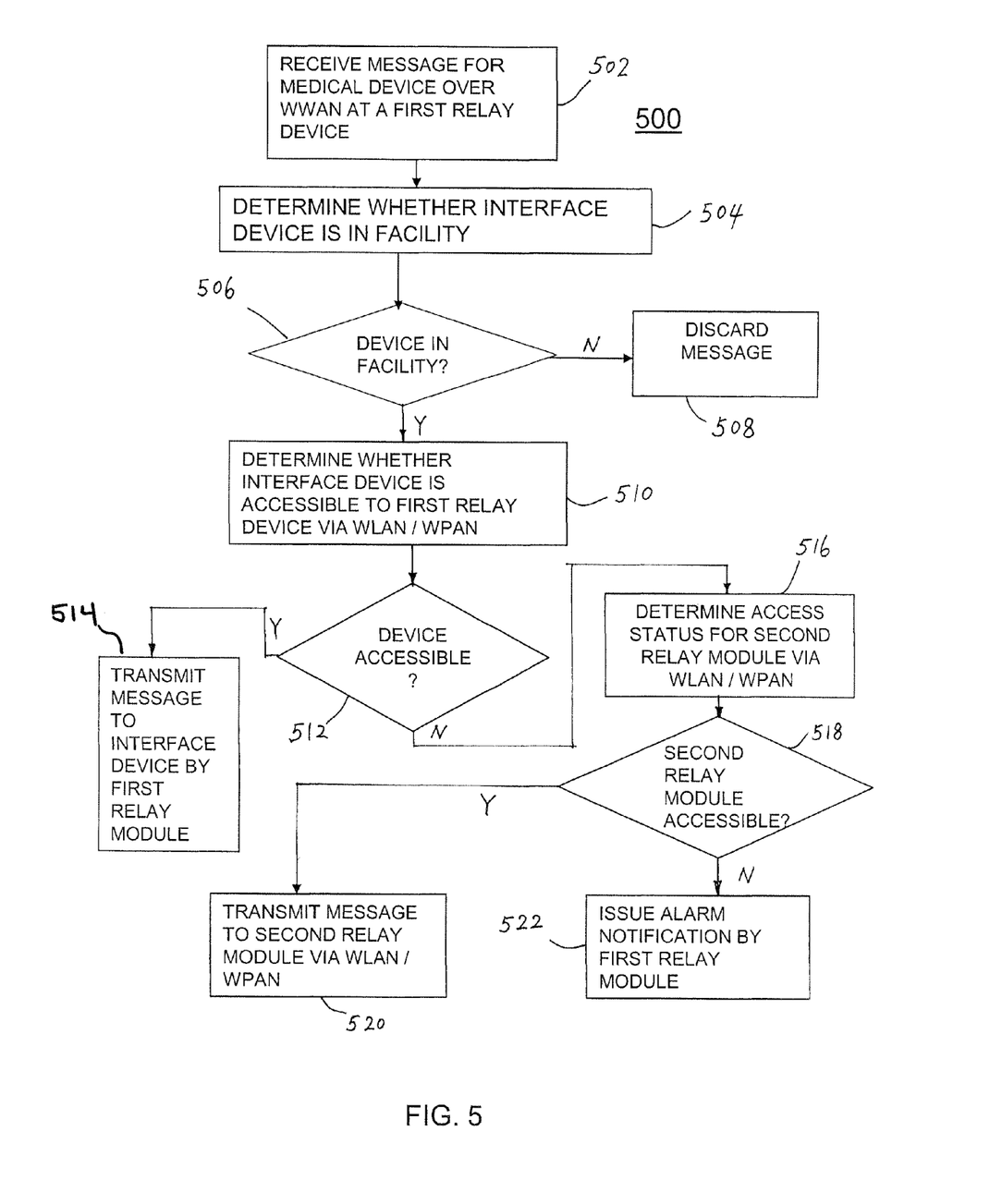
FIG. 5 presents a flow diagram illustrating a second exemplary method of operation for the architecture according to FIG. 1.

FIG. 5 presents a flow diagram illustrating another exemplary method of operation 500 for the architecture according to FIG. 1, relating to the transmission of a message from the access point 40 to be received by one of the medical devices 10. This enables the access point 40, for example, to communicate with medical devices in order to download new firmware or software, to respond to error messages initiated by the medical devices (for example, to re-set a device or remove it from service, or to run device diagnostics), and to operate the medical device (for example, to adjust a flow rate on a feeding pump).

At step 502 of the method 500, the message is received at the first one of the relay modules 30a from the access point 40 via the WWAN. At step 504, the one relay module 30 determines whether the message is intended to reach one of the interface circuits 15 and/or other relay modules 30, 30a located in the facility 20. This may be accomplished, for example, by maintaining a list of active devices 15 and modules 30, 30a in the buffer 35 or in a manner otherwise accessible to the one relay module 30a, or coding an identifier of the interface circuit 15 or module 30, 30a to include an identity of the facility 20 that is stored in the buffer 35 or is otherwise identifiable to the one relay module 30. In the alternative, the received message may include a device identifier such as a serial number or an assigned identifier. Such a received message would then be broadcasted to all or a subset of interface circuits 15 in the facility and each interface circuit 15 determines if it was the intended recipient or should otherwise act upon or ignore the message.

If the one relay module 30a determines at step 506 that the interface circuit 15 or module 30, 30a is not located in the facility, the one relay module 30 may preferably proceed to discard the message at step 508, and/or alternatively alert the access point 40 with a non-delivery message. If the interface circuit 15 is located in the facility 20, the one relay modular 30 determines at step 510 whether the interface circuit 15 or relay module 30, 30a accessible to the one relay device 30 via the WLAN or WPAN (for example, by consulting a list stored in the buffer 35 or that is otherwise accessible to the one relay module 30, or by instructing the transceiver 31 to send a handshake or test transmission directed to the interface circuit 15 and to listen for a reply).

If the one relay module 30a determines at step 512 that the device 15 or relay module 30, 30a is accessible, then at step 514, it transmits the message via network 16 to that device or relay module via the transceiver 31. If the one relay module 30a alternatively determines at step 512 that the device or relay module is not accessible, it proceeds at step 516 to determine whether a second relay module 30, 30a is accessible via the WLAN or WPAN (for example, by instructing the transceiver 31 to send a handshake or test transmission directed to the second relay module and to listen for a reply). If the second relay module 30, 30a is available, then the one relay module 30 forwards the message to the transceiver 31 for transmission to the second relay module 30, 30a over the WLAN or WPAN. If the second relay module 30, 30a is inaccessible, then this portion of the process 500 may preferably be repeated to search for a third relay module 30, 30a that is accessible. Alternatively, or in the event that no other relay module 30, 30a is available, the one relay module 30 may preferably issue an alarm notification at step 522, preferably in one of the same manners described above in reference to the method 400 of FIG. 4.

The novel architecture disclosed herein for providing networked communications between a series of medical devices and a remote monitoring device provides a number of distinct advantages in comparison to other monitoring systems. By employing ZIGBEE networks based on the IEEE 802.15.4 standard according to a preferred embodiment for wireless communications between the medical devices 10 and relay modules 30, 30a, power and size requirements can be minimized so that the interface circuits 15 can be easily and inexpensively applied to and/or integrated with the medical devices 10.

By introducing relay modules 30a that are part of the ZIGBEE networks and are directly able to access off-site monitoring devices via a WWAN, access to and reliance on existing and potentially unreliable LAN facilities at a facility can be avoided. By incorporating relay features into the relay modules 30a that relay communications from a first relay module 30a to a second relay module 30a in the event that WWAN access to the first relay module 30a has been compromised, the present invention improves reliability and enables the use of conventional, low-cost cellular transceivers in the relay modules 30a for accessing the WWAN.

By limiting the configuration of cellular transceivers to just the relay modules 30a, costs can be further reduced. In addition, providing the relay modules 30a in a compact enclosure facilitates the relay modules 30a to be easily connected to reliable commercial power sources and easily moved when needed to reconfigure the ZIGBEE networks according to facilities changes.

It should of course, be understood that while the present invention has been described with respect to disclosed embodiments, numerous variations are possible without departing from the spirit and scope of the present invention as defined in the claims. For example, the present invention may be based on any of a number of current and future WPAN, WLAN and WWAN standards beyond those explicitly described herein. It should also be understood that it is possible to use exclusively relay modules 30 in the WLAN or WPAN network 16 of FIGS. 1 and 2, with transceivers for communicating with other relay modules as well as over the WWAN.

In addition, respective interface circuits useable with the present invention may include components of and perform the functions of the module 30 to provide greater flexibility in accordance with the present invention. Further, numerous configurations of components for relay module 30 are useable with the present invention beyond the components shown in FIG. 3. For instance, an input-output buffer may be used with respective switches under control of a processor for directing medical device data to transceivers 31, 32 as needed. Moreover, it is intended that the scope of the present invention include all other foreseeable equivalents to the elements and structures as described herein and with reference to the drawing figures. Accordingly, the invention is to be limited only by the scope of the claims and their equivalents.

We claim:

1. A system for providing communications between one or more medical devices and a remote device connected to the internet comprising:

at least one interface circuit coupled to one or more of the one or more medical devices and capable of transmitting medical device data using a wireless data connection;

at least two relay modules, each of the at least two relay modules wirelessly coupled to form a mesh network of wireless relay modules, with each of the at least two relay modules comprising:

a first receiver capable of wirelessly receiving medical device data over the wireless data connection;

a first transmitter capable of wirelessly transmitting medical device data to another of the at least two relay modules over the mesh network of wireless-relay modules;

a second transmitter capable of wirelessly transmitting medical device data over an internet-accessible wireless communications network; and a processor coupled to the second transmitter to determine if the internet-accessible wireless communications network is accessible by the second transmitter and coupled to the first transmitter to transmit the medical device data over the mesh network of wireless-relay modules to another of the at least two relay modules if the internet-accessible wireless communications network is not accessible by the second transmitter;

wherein at least one of the at least two relay modules in the mesh network of wireless relay modules is capable of determining an access status of the mesh network of wireless relay modules and providing the access status to the processor for selecting the first or second transmitter for medical device data transmission based upon at least two of: (1) the access status of the mesh network of wireless relay modules; (2) a device status of the one or more medical devices; and (3) a connection status of each of the first and second transmitters in the wireless relay modules;

wherein the connection status of the first transmitter indicates whether the internet accessible wireless communications network is accessible to the wireless relay modules and the connection status of the second transmitter indicates whether the mesh network of wireless relay modules is accessible to the wireless relay modules; and wherein each of the relay modules in the wireless mesh relay network is configured to determine its own current status and to communicate its own current status to each of the other relay modules in the wireless mesh network.

2. The system of claim 1, wherein said processor is configured to determine the connection status of the internet-accessible wireless communications network and transmit medical device data over a communications channel by said second transmitter if said connection status satisfies a particular criteria; and is configured to transmit said medical device data by said first transmitter in communication with said mesh network of wireless relay modules if said connection status fails to satisfy said particular criteria.

3. The system of claim 1, further comprising a second receiver capable of receiving instructions and/or medical device data from said internet-accessible wireless communications network, wherein said first transmitter is further capable of transmitting the instructions and/or medical device data to said at least one medical device.

4. The system of claim 3, wherein said at least two relay modules each comprise:

a memory electrically connected to said processor, said memory capable of buffering said received instructions and/or medical device data destined for respective ones of said medical devices, wherein said processor controls an order and/or priority for transmission of said instructions and/or medical device data to said respective ones of said medical devices.

5. The system of claim 3, wherein said at least two relay modules each comprise:

a memory electrically connected to said processor, said memory capable of buffering said received instructions and/or medical device data destined for respective ones of said medical devices, wherein said processor controls transmission of said instructions and/or medical device data to all or a subset of said medical devices.

6. The system of claim 1, wherein said mesh network of wireless relay modules operates in accordance with a ZIGBEE network protocol.

7. The system of claim 1, wherein said internet-accessible wireless communications network is a mobile communications network.

8. The system of claim 1, wherein said interface circuit comprises:

a transmitter capable of wirelessly transmitting said medical device data over the mesh network of wireless relay modules.

9. The system of claim 1, wherein said interface circuit further comprises: a receiver capable of wirelessly receiving instructions over the mesh network of wireless relay modules for execution by at least one of the one or more medical devices.

10. The system of claim 1 wherein each of the at least two relay modules form a fully connected wireless mesh network of wireless relay modules.

11. The system of claim 1 wherein:

each of the at least two relay modules form a fully connected wireless mesh network of wireless relay modules; and at least one relay module in the wireless mesh network of wireless relay modules is capable of determining the access status of the wireless mesh network of wireless relay modules and providing the access status to the processor for selecting the first or second transmitter for medical device data transmission based upon at least two of: (1) the access status of the wireless mesh network; (2) the device status of the one or more medical devices; and (3) the connection status of each of the first and second transmitters in the wireless relay modules.

12. A process for communicating medical device data from one or more medical devices over a wireless network, the process comprising the steps of:

forming a wireless mesh network from a plurality of relay modules;

receiving at a first relay module via the wireless mesh network medical device data transmitted by at least one interface circuit coupled to a respective medical device;

determining a first relay module status of access by said first relay module to an internet-accessible wireless communications network;

transmitting said medical device data by said first relay module over said internet-accessible wireless communications network when said internet-accessible wireless communications network is accessible, and transmitting said medical device data by said first relay module to a second relay module over the wireless mesh network when said internet-accessible wireless communications network is not accessible;

wherein at least one relay module in the wireless mesh network is capable of determining an access status of the mesh network of wireless relay modules and providing the access status to a processor of the first relay module for selecting a first or second transmitter for medical data transmission based upon at least two of: (1) the access status of the mesh network of wireless relay modules; (2) a device status of the one or more medical devices; and (3) a connection status of each of the first and second transmitters in the wireless relay modules;

the connection status of the first transmitter indicates whether the internet accessible wireless communications network is accessible to the first wireless relay module and the connection status of the second transmitter indicates whether the wireless mesh network is accessible to the first wireless relay module; and each of the relay modules in the wireless mesh network is configured to determine its own current status and to communicate its own current status to each of the other relay modules in the wireless mesh network.

13. The process of claim 12, further comprising:

determining a second relay module status of access by said second relay module to the internet-accessible wireless communications network;

transmitting said medical device data by said second relay module over said internet-accessible wireless communications network when said second relay module is able to access the internet-accessible wireless communications network, and transmitting said medical device data by said second relay module to a third relay module over the wireless mesh network when said second relay module is not able to access the internet-accessible wireless communications network.

14. The process of claim 12 further comprising:

receiving medical device instructions and/or said medical device data over the internet-accessible wireless communications network intended for at least one of said medical devices; and transmitting said received instructions and/or said medical device data via at least a first relay module to said intended at least one of said medical devices.

15. The process of claim 14 further comprising:

buffering by said first relay module said received instructions and/or medical device data destined for respective ones of the medical devices; and controlling an order and/or priority of transmitting said instructions and/or medical device data to said respective ones of the medical devices.

16. The process of claim 14 further comprising:

transmitting said received instructions and/or medical device data destined for respective ones of the medical devices to all or a subset of all of the medical devices.

17. The process of claim 12 further comprising:

providing an indication of potential communications over said internet-accessible wireless communications network during a power-up sequence of said first relay module.

18. The process of claim 12 further comprising:

providing an indication of potential communications over said wireless mesh network during a power-up sequence of said first relay module.

19. The process of claim 12, wherein said wireless mesh network operates in accordance with a ZIGBEE network protocol.

20. The process of claim 12, wherein said wireless mesh network is a relay enabled Bluetooth network.

21. The process of claim 12, wherein said internet-accessible wireless communications network comprises a communications channel of a mobile communications network.

22. The process of claim 21, wherein said internet-accessible wireless communications network operates in accordance with one of: a CDMA network protocol; or a GSM-based network protocol.

23. The process of claim 12, wherein determining the first relay module status of access further comprises:

measuring a state of said wireless mesh network; and determining said status of access of said wireless mesh network as a function of said measured state of said wireless mesh network.

24. The process of claim 12, wherein said first relay module status of access is determined as a function of a value stored by a storage element of said first relay module.

25. A system comprising:

at least one medical device, each of said at least one medical devices having at least one interface circuit coupled thereto, with each of said at least one interface circuits configured to receive medical device data from at least one of said at least one medical devices and configured to transmit medical device data provided thereto using a wireless data connection; and at least two relay modules, each of the at least two relay modules wirelessly coupled to each of said at least one medical devices via respective interface circuits such that each of said at least two relay modules and at least some of said at least one medical device form a wireless mesh relay network over which each of said at least two relay modules are capable of wirelessly receiving medical device data transmitted by one or more of said interface circuit and wherein at least one relay module is capable of determining an access status of the wireless mesh relay network and selecting a wireless communication path for medical device data transmission and wherein at least one of the at least two relay modules is capable of transmitting medical device data provided thereto over an internet accessible wireless communications network and wherein each of the at least two relay modules selects the wireless communication path based upon at least two of:

(1) the access status of the wireless mesh relay network;
(2) a device status for each of the at least one medical devices; and
(3) a connection status of the at least one relay module to the internet accessible wireless communications network;

wherein the connection status comprises:

a first connection status which indicates whether the internet accessible wireless communications network is accessible by the wireless relay modules; and a second connection status indicates whether the wireless mesh relay network is accessible by the wireless relay module; and wherein each of the relay modules in the wireless mesh relay network is configured to determine its own current status and to communicate its own current status to each of the other relay modules in the wireless mesh relay network.

26. The system of claim 25 wherein:

each of the relay modules in the wireless mesh relay network is configured to determine its own current status and to communicate its own current status to each of the other relay modules in the wireless mesh relay network; and each of the relay modules in the wireless mesh relay network is configured to receive said own current status of each of the other relay modules in the wireless mesh relay network.

27. The system of claim 25 wherein at least one of the relay modules comprises:
- a first transceiver capable of wirelessly receiving medical device data transmitted by each of said at least one interface circuits and capable of wirelessly transmitting medical device data to another of the relay modules in the wireless mesh relay network;
- a second transceiver capable of wirelessly transmitting medical device data over the internet-accessible wireless communications network; and
- a processor coupled to the first and second transceivers and configured to determine if the wireless mesh relay network is accessible by the first transceiver of the relay modules and to determine if the internet-accessible wireless communications network is accessible by the second transceiver of the relay modules.

28. The system of claim 27 wherein in response to the internet-accessible wireless communications network not being accessible by the second transceiver, the first transceiver transmits the medical device data over the wireless mesh relay network to another of the at least two relay modules comprising the wireless mesh relay network.

* * * * *